United States Patent
Magar et al.

(10) Patent No.: US 8,611,319 B2
(45) Date of Patent: Dec. 17, 2013

(54) METHODS AND APPARATUS TO RETROFIT WIRED HEALTHCARE AND FITNESS SYSTEMS FOR WIRELESS OPERATION

(75) Inventors: Surendar Magar, Dublin, CA (US); Louis Yun, Los Altos, CA (US); James Beck, Berkeley, CA (US); Venkateswara R. Sattiraju, Union City, CA (US); Ali Niknejad, Berkeley, CA (US)

(73) Assignee: Hmicro, Inc., Los Altos, CA (US)

(*) Notice: Subject to any disclaimer, the term of this patent is extended or adjusted under 35 U.S.C. 154(b) by 86 days.

(21) Appl. No.: 12/739,519

(22) PCT Filed: Oct. 23, 2008

(86) PCT No.: PCT/US2008/081010
§ 371 (c)(1), (2), (4) Date: Oct. 8, 2010

(87) PCT Pub. No.: WO2009/055608
PCT Pub. Date: Apr. 30, 2009

(65) Prior Publication Data
US 2011/0019595 A1    Jan. 27, 2011

Related U.S. Application Data

(60) Provisional application No. 60/982,288, filed on Oct. 24, 2007.

(51) Int. Cl.
*H04W 4/00* (2009.01)
*G08B 1/08* (2006.01)
*A61B 5/00* (2006.01)

(52) U.S. Cl.
USPC ............... 370/338; 600/300; 340/539.12

(58) Field of Classification Search
None
See application file for complete search history.

(56) References Cited

U.S. PATENT DOCUMENTS

| | | | |
|---|---|---|---|
| 5,231,990 | A | 8/1993 | Gauglitz |
| 5,511,553 | A | 4/1996 | Segalowitz |
| 5,717,848 | A | 2/1998 | Watanabe et al. |
| 5,720,770 | A | 2/1998 | Nappholz et al. |
| 5,913,727 | A | 6/1999 | Ahdoot |

(Continued)

FOREIGN PATENT DOCUMENTS

| | | |
|---|---|---|
| EP | 1292218 B1 | 4/2006 |
| GB | 2420628 A | 5/2006 |

(Continued)

OTHER PUBLICATIONS

European search report dated Apr. 5, 2012 for EP Application No. 08841472.7.

(Continued)

*Primary Examiner* — Xavier S. Wong
(74) *Attorney, Agent, or Firm* — Wilson Sonsini Goodrich & Rosati

(57) ABSTRACT

Provided herein is an apparatus for converting a wired sensor system to a wireless sensor system. The apparatus can comprise a relay station comprising at least one antenna and at least one radio. The relay station can be adaptable to be integrated as at least one application specific integrated circuit and further adaptable to convert a wired sensor system into a wireless sensor system. Further provided are systems for converting wired sensor systems into wireless sensor systems and methods of use.

33 Claims, 5 Drawing Sheets

(56) References Cited

U.S. PATENT DOCUMENTS

| | | | |
|---|---|---|---|
| 5,957,854 A | 9/1999 | Besson et al. | |
| D439,981 S | 4/2001 | Kasabach et al. | |
| 6,230,970 B1 | 5/2001 | Walsh et al. | |
| 6,275,143 B1 | 8/2001 | Stobbe | |
| 6,278,499 B1 | 8/2001 | Darbee et al. | |
| 6,295,461 B1 | 9/2001 | Palmer et al. | |
| D451,604 S | 12/2001 | Kasabach et al. | |
| 6,336,900 B1 | 1/2002 | Alleckson et al. | |
| D460,971 S | 7/2002 | Sica et al. | |
| 6,436,058 B1 | 8/2002 | Krahner et al. | |
| 6,463,039 B1* | 10/2002 | Ricci et al. | 370/277 |
| 6,494,829 B1 | 12/2002 | New et al. | |
| 6,527,711 B1 | 3/2003 | Stivoric et al. | |
| 6,595,929 B2 | 7/2003 | Stivoric et al. | |
| 6,605,038 B1 | 8/2003 | Teller et al. | |
| 6,677,852 B1 | 1/2004 | Landt | |
| 6,694,180 B1 | 2/2004 | Boesen | |
| 6,731,962 B1 | 5/2004 | Katarow et al. | |
| 6,885,191 B1 | 4/2005 | Gleman | |
| 6,893,396 B2 | 5/2005 | Schulze et al. | |
| 6,909,420 B1 | 6/2005 | Nicolas et al. | |
| 7,020,508 B2 | 3/2006 | Stivoric et al. | |
| 7,125,382 B2 | 10/2006 | Zhou et al. | |
| 7,206,630 B1 | 4/2007 | Tarler | |
| 7,270,633 B1 | 9/2007 | Goscha et al. | |
| 7,294,105 B1 | 11/2007 | Islam | |
| 7,376,234 B1 | 5/2008 | Gardiner | |
| 7,382,247 B2 | 6/2008 | Welch et al. | |
| 7,571,369 B2 | 8/2009 | Wang et al. | |
| 7,602,301 B1 | 10/2009 | Stirling et al. | |
| 7,603,255 B2 | 10/2009 | Case et al. | |
| 7,733,224 B2 | 6/2010 | Tran | |
| 7,969,307 B2 | 6/2011 | Peeters | |
| 2001/0003163 A1 | 6/2001 | Bungert et al. | |
| 2001/0047127 A1 | 11/2001 | New et al. | |
| 2002/0065828 A1 | 5/2002 | Goodspeed | |
| 2003/0219035 A1 | 11/2003 | Schmidt | |
| 2003/0236103 A1* | 12/2003 | Tamaki et al. | 455/552.1 |
| 2004/0013097 A1 | 1/2004 | Massa | |
| 2004/0077975 A1 | 4/2004 | Zimmerman | |
| 2004/0199056 A1 | 10/2004 | Husemann et al. | |
| 2005/0035852 A1 | 2/2005 | Paulsen | |
| 2005/0113167 A1 | 5/2005 | Buchner et al. | |
| 2005/0119533 A1 | 6/2005 | Sparks et al. | |
| 2005/0206518 A1 | 9/2005 | Welch et al. | |
| 2005/0282633 A1 | 12/2005 | Nicolas et al. | |
| 2006/0031102 A1 | 2/2006 | Teller et al. | |
| 2006/0122473 A1 | 6/2006 | Kill et al. | |
| 2006/0122474 A1 | 6/2006 | Teller et al. | |
| 2006/0264767 A1 | 11/2006 | Shennib | |
| 2007/0027388 A1* | 2/2007 | Chou | 600/393 |
| 2007/0087780 A1 | 4/2007 | Nassimi | |
| 2007/0100219 A1 | 5/2007 | Sweitzer et al. | |
| 2007/0135866 A1 | 6/2007 | Baker et al. | |
| 2007/0208233 A1 | 9/2007 | Kovacs | |
| 2007/0208262 A1 | 9/2007 | Kovacs | |
| 2007/0232234 A1* | 10/2007 | Inzerillo et al. | 455/42 |
| 2007/0244383 A1 | 10/2007 | Talbot et al. | |
| 2007/0279217 A1 | 12/2007 | Venkatraman et al. | |
| 2007/0282218 A1 | 12/2007 | Yarden | |
| 2008/0001735 A1 | 1/2008 | Tran | |
| 2008/0054880 A1 | 3/2008 | Miyauchi et al. | |
| 2008/0065877 A1 | 3/2008 | Son et al. | |
| 2008/0119707 A1 | 5/2008 | Stafford | |
| 2008/0139894 A1 | 6/2008 | Szydlo-Moore et al. | |
| 2009/0037670 A1 | 2/2009 | Rofougaran | |
| 2009/0051544 A1 | 2/2009 | Niknejad | |
| 2009/0054737 A1 | 2/2009 | Magar et al. | |
| 2009/0316618 A1* | 12/2009 | Fielding et al. | 370/316 |
| 2010/0013607 A1* | 1/2010 | Sabo et al. | 340/286.06 |
| 2010/0049006 A1 | 2/2010 | Magar et al. | |
| 2010/0160746 A1 | 6/2010 | Venkatraman et al. | |
| 2010/0316043 A1* | 12/2010 | Doi et al. | 370/350 |
| 2011/0019824 A1 | 1/2011 | Sattiraju et al. | |

FOREIGN PATENT DOCUMENTS

| | | |
|---|---|---|
| JP | 2006055530 A | 3/2006 |
| KR | 10-2004-0032451 | 4/2004 |
| KR | 10-2004-0074056 | 8/2004 |
| KR | 10-2005-0072558 | 7/2005 |
| KR | 10 2005-0116274 | 12/2006 |
| KR | 10-2007-0048168 | 5/2007 |
| WO | WO 89/02682 A1 | 3/1989 |
| WO | WO 89/04093 A1 | 5/1989 |
| WO | WO 89/04578 A1 | 5/1989 |
| WO | WO 98/10617 A1 | 3/1998 |
| WO | WO 2002/064032 A2 | 8/2002 |
| WO | WO 03/015005 A2 | 2/2003 |
| WO | WO 03/015838 A2 | 2/2003 |
| WO | WO 2002/064032 A3 | 2/2003 |
| WO | WO 03/015005 A3 | 12/2003 |
| WO | WO 2004/002301 A2 | 1/2004 |
| WO | WO 03/015838 A3 | 4/2004 |
| WO | WO 2004/002301 A3 | 4/2004 |
| WO | WO 03/015838 A3 | 5/2004 |
| WO | WO 2004/084720 A2 | 10/2004 |
| WO | WO 2004/084720 A3 | 3/2005 |
| WO | WO 2005/029242 A2 | 3/2005 |
| WO | WO 2005/029242 A3 | 6/2005 |
| WO | WO 2006/094513 A2 | 9/2006 |
| WO | WO 2006/094513 A3 | 4/2007 |
| WO | WO 2008/035151 A2 | 3/2008 |
| WO | WO 2008/097316 A1 | 8/2008 |
| WO | WO 2008/035151 A3 | 12/2008 |

OTHER PUBLICATIONS

Berrou, et al. Near Shannon limit error-correcting coding and decoding: Turbo-codes. 1. IEEE Int. Conf. Commun., vol. 2, Geneva, Switzerland, May 1993, p. 1064-1070.

International Search Report and written opinion dated Mar. 19, 2009 for PCT application No. 2008/073739.

International search report and written opinion dated Nov. 19, 2007 for PCT application No. 2007/062772.

International search report and written opinion dated Jan. 22, 2009 for PCT application No. 2008/080716.

International search report and written opinion dated Feb. 24, 2009 for PCT application No. 2008/073591.

International search report and written opinion dated Apr. 24, 2009 for PCT application No. 2008/081010.

Montemont, et al. Experimental comparison of discrete and CMOS charge sensitive preamplifiers for CZT radiation detectors. IEEE Transactions on Nuclear Science. 2002; 50(4):936-941.

UK combined search and examination report dated Sep. 12, 2011 for Application No. GB0815326.4.

Vucetic, et al. Turbo Codes: Principles and Applications. The Kluwer International Series in Engineering and Computer Science). Kluwer Academic Publishers, 2000. (Table of Contents pages only) (8 pages).

UK combined search and examination report dated Jun. 26, 2012 for Application No. GB 1210339.6.

UK combined search and examination report dated Jun. 27, 2012 for Application No. GB 1210351.1.

Office action dated Feb. 24, 2011 for U.S. Appl. No. 12/193,865.
Office action dated Mar. 29, 2012 for U.S. Appl. No. 12/739,549.
Office action dated Apr. 4, 2013 for U.S. Appl. No. 12/702,127.
Office action dated May 2, 2011 for U.S. Appl. No. 12/134,151.
Office action dated Jun. 21, 2012 for U.S. Appl. No. 12/193,865.
Office action dated Jul. 9, 2013 for U.S. Appl. No. 12/096,195.
Office action dated Aug. 7, 2009 for U.S. Appl. No. 11/756,161.
Office action dated Oct. 5, 2012 for U.S. Appl. No. 12/739,549.
Office action dated Nov. 28, 2011 for U.S. Appl. No. 12/193,865.
Office action dated Dec. 19, 2011 for U.S. Appl. No. 12/134,151.
Office action dated Aug. 13, 2013 for U.S. Appl. No. 12/193,865.

* cited by examiner

METHODS AND APPARATUS TO RETROFIT WIRED HEALTHCARE AND FITNESS SYSTEMS FOR WIRELESS OPERATION

CROSS-REFERENCE

This application claims the benefit of U.S. Provisional Application No. 60/982,288, filed Oct. 24, 2007, which application is incorporated herein by reference.

BACKGROUND OF THE INVENTION

While many other systems have gone wireless, the majority of healthcare and fitness monitoring system remain wired today. A typical wired healthcare system is shown in FIG. 1. The system shown in FIG. 1 can be used to monitor a variety of physiological parameters such as electrocardiogram (ECG), electroencephalogram (EEG), electromyogram (EMG), blood glucose, blood pressure, heart rate, blood oxygen saturation ($SpO_2$), hydration, air flow, pressure, acceleration and temperature. In the system shown, the sensors are placed on the subject's body to measure the desired physiological parameters. These sensors are connected to an anchor medical device which is called the host in the system. The host device can be any healthcare related device such as a bedside patient monitor, holster monitor, glucose meter, EEG system, blood pressure monitor, and/or a mobile health monitor. The host can be a stationary platform, a portable device or a mobile device. As shown, the wired sensor system typically feeds the data to the host via a wired host bus. The type of host bus is defined during the initial design of the healthcare system.

The tethering of patients to healthcare systems creates many problems today. The leads connected to sensors are reused among various patients often causing infection, leading to even death in many cases. Wires also come in the way of clinicians and caretakers resulting in lower productivity, poorer quality of care and lower reliability as wires frequently come off. Furthermore, tethering is a major discomfort for patients, particularly when extended monitoring is involved. Due to these and many other reasons, it would be desirable to make healthcare monitoring systems totally wireless, thereby untethering patients from host systems.

There is a large installed base of a variety of host systems with tethered sensors—bedside patient monitors in hospitals and clinics; portable host devices for ambulatory monitoring (such as holter monitors). It is highly desirable to retrofit these legacy systems for wireless monitoring. For wireless monitoring to be widespread, the retrofitted wireless scheme must be able to compete with the wired systems in every way. The wireless link must be as reliable as a wire. The wireless sensors attached to the body must be ultra low cost, must dissipate very low power for multi day operation, and must be physically small and disposable. Furthermore, the wireless adaptor plugged into host system must be compact, low power, and low cost.

There have been recent attempts to create wireless systems some of which have been introduced in the market. However, all these systems have wireless sensors, host systems and adaptors which are bulky, high power, expensive and have questionable reliability. It makes them unsuitable to compete with wired solutions for large scale deployment. The invention described herein proposes a scheme to retrofit the existing wired systems for wireless operation based on integrated semiconductor solutions with attributes to compete with today's wired systems to meet the mass market needs. The proposed scheme transforms the wired system as shown in FIG. 1 to a wireless system in a transparent manner and without an impact on the core infrastructure of the system, including the host's hardware or software, also known as retrofitting.

SUMMARY OF THE INVENTION

Provided herein is an apparatus for converting a wired sensor system to a wireless sensor system. The apparatus can comprise a relay station comprising at least one antenna and at least one radio. The relay station can be adaptable to be integrated as at least one application specific integrated circuit and further adaptable to convert a wired sensor system into a wireless sensor system. Furthermore, the relay station can further comprise a transcoder. The transcoder can be adaptable to demultiplex data received by the relay station, data to be sent to the relay station, or data communicated to the relay station. Additionally, the relay station can further comprise a host interface unit adaptable to transmit data from the relay station to a host device using a host device bus scheme. The host bus scheme can be selected from at least one of a universal serial bus (USB), a mini universal serial bus (mini USB), a secure digital, a mini secure digital, a peripheral component interconnect (PCI), a mini peripheral component interconnect (a mini PCI), an analog bus, or any suitable combination thereof. In some embodiments, the apparatus can further comprise a connector adaptable to communicate with a host device. The connector can comprise a bus adaptable to be in communication with the host device. The relay station can further comprise more than one radio. In addition, the relay station can be further adaptable to be in communication with a wireless patch adaptable be integrated with at least one application specific integrated circuit. The relay station can be further adaptable to transmit data from a wireless sensor to a host device. Alternatively, the relay station can be further adaptable to transmit data from a host device to a wireless sensor. In some embodiments, the relay station is adaptable to use at least one host radio to wirelessly send data received from the sensors to a host having wireless connectivity with the relay station. The host radio can be adaptable to use at least one of radio scheme wherein the at least one radio scheme is selected from Wi-Fi, Bluetooth, ZigBee, wireless medical telemetry service (WMTS), medical implant communications service (MICS), a narrowband radio, or an ultrawideband radio.

Further provided herein is an apparatus for converting a wired sensor system to a wireless sensor system comprising: a relay station comprising at least one antenna, the relay station adaptable to convert a wired sensor system into a wireless sensor system; and at least two complementary radios, each complementary radio having an antenna. The at least two complementary radios are Ultrawideband and narrowband radios. The two complementary radios can be adaptable to operate in a low power mode and a high power mode. Furthermore, the at least two complementary radios are adaptable to operate in a short range mode and a high range mode. The relay station can be adaptable to be in communication with two different radios. The two complementary radios can also make the wireless link reliable and robust through radio diversity. There is a high probability that one of the complementary radios will be operational when the other suffers an outage due to multipath fading or interference.

Further provided herein is a system integrated as at least one application specific integrated circuit for converting a wired sensor system to a wireless sensor system comprising: a relay station adaptable to convert a wired sensor system to a wireless sensor system; and at least one wireless patch comprising a wireless sensor and at least one radio, wherein the relay station is adaptable to convert a wired sensor system to a wireless sensor system. The at least one wireless patch can further comprise an analog to digital converter. In some embodiments, more than one wireless patch can communicate with the relay station, the relay station adaptable to receive more than one signal. The radio can multiplex the more than one signal to transmit the signal.

Methods of detecting a signal are also provided herein. Disclosed is a method of detecting a signal using a wireless sensor system comprising: (a) detecting at least one signal from a signal source; (b) transmitting the signal in digital format to a relay station comprising at least one antenna and at least one radio, the relay station integrated as at least one application specific integrated circuit and further adaptable to convert a wired sensor system into a wireless sensor system; (c) processing the data received with the relay station; and (d) transmitting the processed data to a host device. The at least one signal can be an analog signal. The method can further comprise the step of converting the analog signal to a digital signal prior to the transmitting step. Additionally, the method can further comprise the step of converting the digital signal to an analog signal prior to the transmitting step.

Further provided herein is a method of retrofitting a wired healthcare system into a wireless healthcare system comprising: retrofitting a wired healthcare system with an adapter member in communication with a wired healthcare system, the adapter member comprising at least one antenna and at least one radio, wherein the adapter member is adaptable to be integrated as at least one application specific integrated circuit and further adaptable to convert a wired healthcare system into a wireless healthcare system. The method can further comprise the step of applying at least one wireless patch to a patient, the wireless patch adaptable to detect a physiological parameter and further adaptable to communicate with the adapter member.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
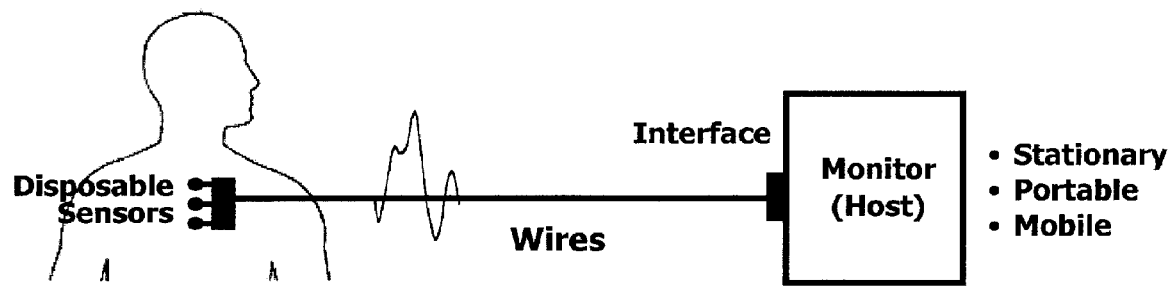
FIG. 1 is a schematic illustration showing the components of a wired healthcare system.

Provided herein is a system for retrofitting a wired sensor system into a wireless sensor system by attaching an adapter device to the sensor system to be modified. Further provided herein is a method for retrofitting a wired system into a wireless system by connecting the sensor to the host system via a host bus without impacting the hardware or software of the system. The concept of retrofitting a wired healthcare system has been previously described in foreign application PCT/US07/62772, filed on Feb. 23, 2007, U.S. application Ser. No. 12/134,151, filed on Jun. 5, 2008, and U.S. Ser. Nos. 60/968,023 filed on Aug. 21, 2007, which are herein incorporated by reference in their entirety.

Provided herein is an apparatus for converting a wired sensor system to a wireless sensor system. The apparatus can comprise a relay station comprising at least one antenna and at least one radio. The relay station can be adaptable to be integrated as at least one application specific integrated circuit and further adaptable to convert a wired sensor system into a wireless sensor system. Furthermore, the relay station can further comprise a transcoder. The transcoder can be adaptable to demultiplex data received by the relay station, data to be sent to the relay station, or data communicated to the relay station. Additionally, the relay station can further comprise a host interface unit adaptable to transmit data from the relay station to a host device using a host device bus scheme. The host bus scheme can be selected from at least one of a universal serial bus (USB), a mini universal serial bus (mini USB), a secure digital, a mini secure digital, a peripheral component interconnect (PCI), a mini peripheral component interconnect (a mini PCI), an analog bus, or any suitable combination thereof. In some embodiments, the apparatus can further comprise a connector adaptable to communicate with a host device. The connector can comprise a bus adaptable to be in communication with the host device. The relay station can further comprise more than one radio. In addition, the relay station can be further adaptable to be in communication with a wireless patch adaptable be integrated with at least one application specific integrated circuit. The relay station can be further adaptable to transmit data from a wireless sensor to a host device. Alternatively, the relay station can be further adaptable to transmit data from a host device to a wireless sensor. In some embodiments, the relay station is adaptable to use at least one host radio to wirelessly send data received from the sensors to a host having wireless connectivity with the relay station. The host radio can be adaptable to use at least one of radio scheme wherein the at least one radio scheme is selected from Wi-Fi, Bluetooth, ZigBee, wireless medical telemetry service (WMTS), medical implant communications service (MICS), a narrowband radio, or an ultrawideband radio.

Further provided herein is an apparatus for converting a wired sensor system to a wireless sensor system comprising: a relay station comprising at least one antenna, the relay station adaptable to convert a wired sensor system into a wireless sensor system; and at least two complementary radios, each complementary radio having an antenna. The at least two complementary radios are ultrawideband narrowband radios. The two complementary radios can be adaptable to operate in a low power mode and a high power mode. Furthermore, the at least two complementary radios are adaptable to operate in a short range mode and a high range mode. The relay station can be adaptable to be in communication with two different radios. The two complementary radios also make the wireless link reliable and robust through radio diversity. There is a high probability that one of the complementary radios will be operational when the other suffers an outage due to multipath fading or interference. The concept of complementary radio based communication has been previously described in a foreign application, PCT/

US08/003088, filed on Mar. 7, 2008, U.S. Provisional Application Ser. No. 60/894,174, filed on Mar. 9, 2007, and U.S. Provisional Application Ser. No. 60/894,093, filed on Mar. 9, 2007, which are incorporated herein in their entirety.

I. Devices

Figure 2:
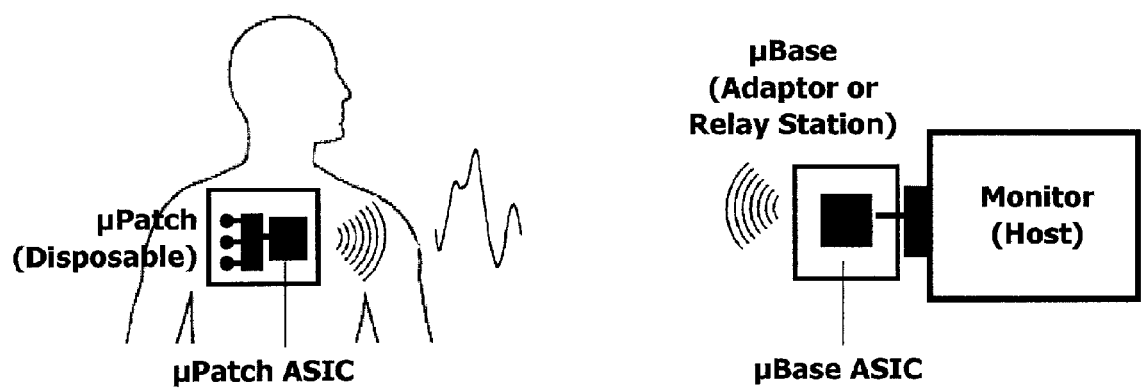
FIG. 2 is a schematic illustration showing the components of a wireless healthcare system.

FIG. 1 shows a wired healthcare or fitness system. The wired sensor system can comprise leads in communication with a patient and a host. The host can be stationary, portable, or mobile, or any combination thereof. The host can be in communication with the patient through a host but. The host can further be in communication with an optional network and server. The wired system of FIG. 1 can be retrofitted for wireless operation as shown in FIG. 2 by using a wireless sensor system. FIG. 2 illustrates a wireless sensor system for use with a healthcare and/or fitness system. The wireless sensor system comprises patches, for example, micropatches (μpatches), as shown in the figure. The micropatches can be in wireless communication with a relay station, indicated as microbase (μbase) in the figure. The microbase can be in communication with a host through a host bus. The host can be stationary, portable, or mobile, or any combination thereof. The host can then be in communication with an optional network and server. The system utilizes wireless sensors in the form of micropatches that are placed on the body of subject. The micropatches comprise the same type of basic sensors as used in the wired system. In addition, the micropatches comprise a radio system that can transmit the data to a base device as shown in FIG. 2. The base is attached to the host device of the healthcare system that needs to be made wireless. Instead of using wired links between the patches and the base, the system can now wirelessly receive physiological data from a subject's body. This can provide the subject with increased mobility while providing the same functionality as a wired system.

Figure 3:
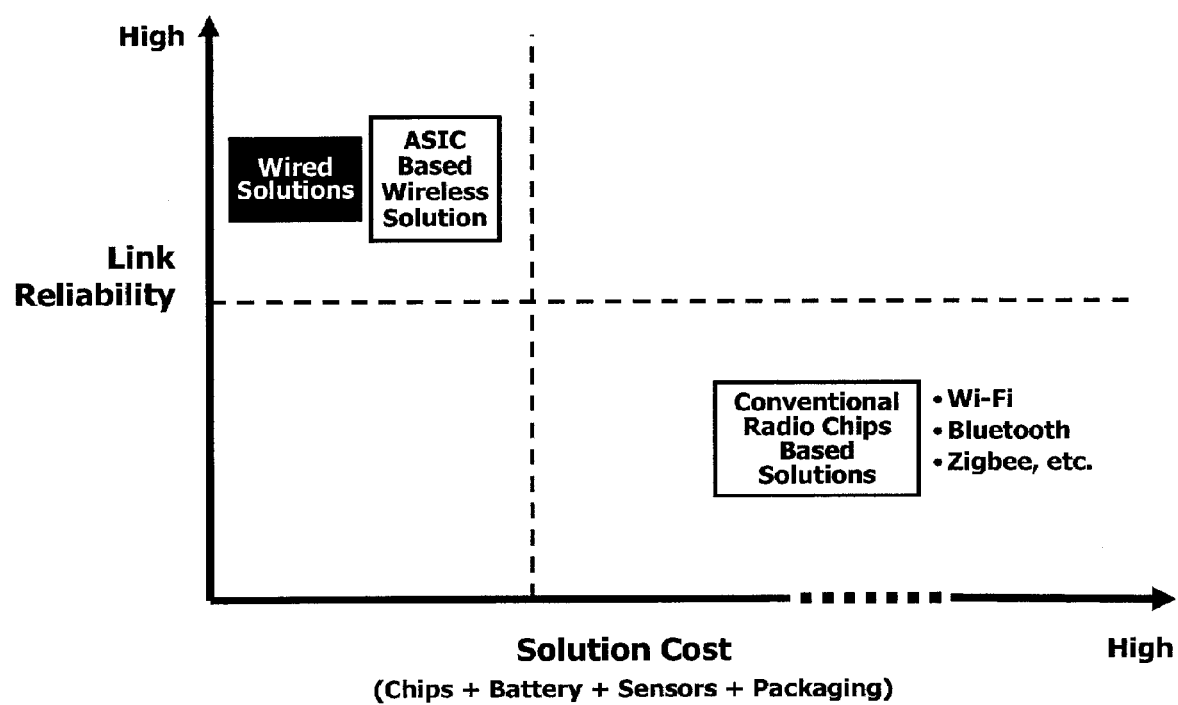
FIG. 3 is a graph illustrating the attributes of wired and wireless systems.

Provided herein is a system for retrofitting a wired sensor system using application specific integrated circuits (ASIC). The invention disclosed herein further comprises micropatches and microbases using application specific integrated circuit (ASIC) devices. The use of ASIC with the system facilitates the economics and size/power advantages of semiconductor technology for large scale deployment. FIG. 3 is a graph illustrating the attributes of highly integrated ASIC technology for wireless solutions to compete with today's wired solutions. As shown in FIG. 3, currently, reference points are established by wired solutions in terms of low cost and high link reliability for application capable of continuous monitoring. FIG. 3 also illustrates the combinations possible with standard radio chips, based on conventional radio chips combined with other chips to support sensor signal processing. The possible combination can require the use of many chips, which can make such combinations expensive, bulky, and/or requiring large amounts of power resulting in the need for a larger battery. Furthermore, wireless link reliability of conventional systems can be relatively low compared to conventional consumer grade radios which are not designed for sensitive healthcare applications. The combinations can not enable high volume applications served by wired solutions today.

Therefore, optimal solutions can be developed using highly integrated ASIC designs that can combine a high reliability robust radio with other needed functions including, but not limited to, sensor signal processing circuits. In some embodiments, the architectures of micropatch ASIC and microbase ASIC can be been defined as a set. In such an embodiment, a high reliability radio can be designed by asymmetrically distributing the cost and/or power between to the micropatch ASIC and microbase ASIC. The requirements of the micropatches can be more stringent than the requirements of the microbases. Using an ASIC chipset, it can becomes possible to push the cost and power from the micropatch ASIC to the microbase ASIC. Technologies along these lines have been disclosed in the patent applications referenced herein.

Figure 4:
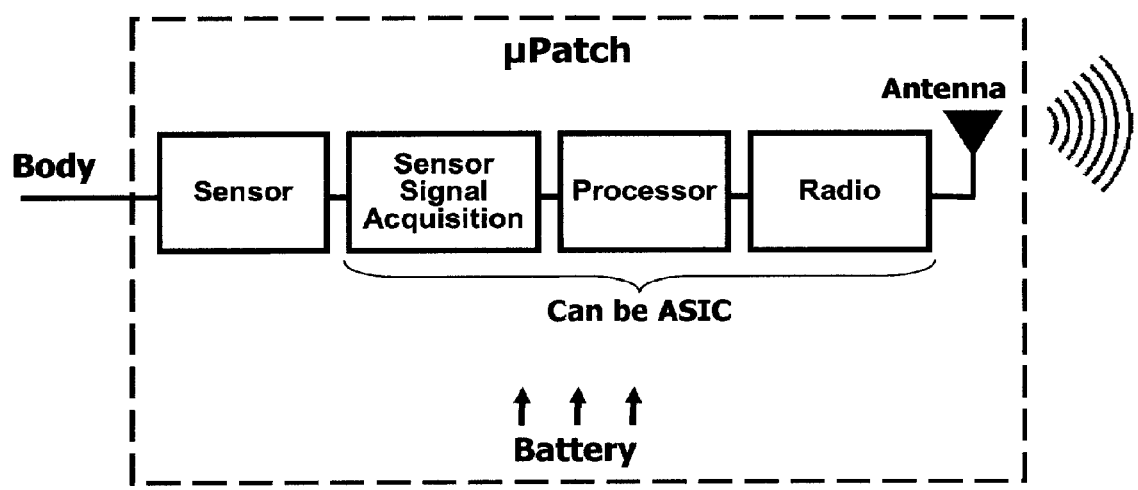
FIG. 4 is an illustration of one embodiment of a wireless sensor or micropatch.

FIG. 4 is illustrates a high level block diagram of an ASIC that can be used with a micropatch. The microbase or relay station can act as a bridge between the micropatch and the host device for retrofitting. The microbase can receive data from the micropatch and can then rearrange the data as needed to present it to the host. The microbase can present the data to the host using the host bus, in the same way as the host was receiving data from the wired sensors (as shown in FIG. 1).

Figure 5:
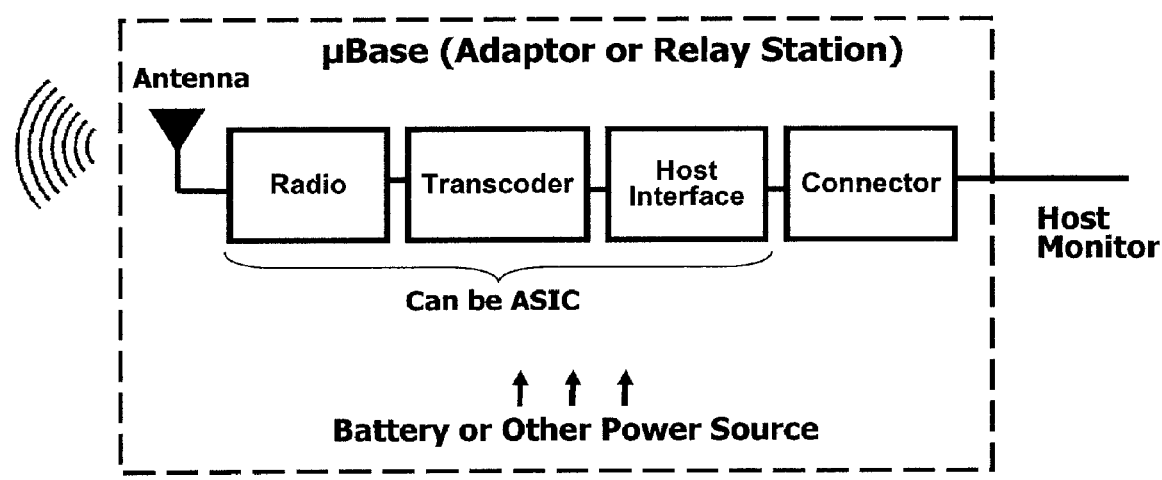
FIG. 5 is an illustration of one embodiment of a relay station and related components.

FIG. 5 illustrates one embodiment of a functional diagram of a relay station. The relay station can be largely implemented on an ASIC. The relay station can be in communication with the micropatches through a wireless link. In one embodiment, the relay station can be comprised of an antenna, a radio, a transcoder, and a host interface unit (I/F). A connector in communication with the relay station can also be in communication with a host. The connector can be in communication with the host through a bus. On one end of the base, the base can wirelessly communicates with the micropatches through at least one an antenna. Additionally, the base can communicate with the micropatches using at least one radio. The base can be designed to work with any suitable radio scheme including, but not limited to WiFi, Bluetooth, ZigBee, ultrawideband (UWB), medical implant communications service (MICS), wireless medical telemetry service (WMTS), any suitable narrowband radio, any other suitable standard or proprietary based radio, or combination thereof.

Traditional wired healthcare systems utilize sensors positioned on the body of a patient which are directly connected to a host device using wires. Traditional wired healthcare systems include electrocardiogram (ECG), electroencephalogram (EEG), and electromyogram (EMG) systems. In those systems, the host device accepts the analog signal that is detected by the sensors. The host typically accepts multiple such analogue signals in parallel from multiple leads. For example, ECG systems can use three, five, seven, or twelve leads. Therefore, the host device can an have an analog bus that can accept multiple parallel analog signals, or an analog lead for accepting a single analog signal. Wireless sensor systems, as provided herein, can use a digital radio to send the sensor data from the micropatches to the base. The analog signal from the sensor can be converted into a digital format through one or more analog to digital (A/D) converters. The digital data is then sent to the radio on the micropatch. The radio can then send the information from the sensor to the base. In some embodiments, the radio transmits the information from one sensor. In some embodiments, the radio transmits data from several body sensors to the base. The micropatch radio can multiplex several sensor signals using a multiplexing scheme, such as, time, frequency, or code multiplexing.

The data received by the base radio can then pass through a transcoder on the base. The transcoder can function to rearrange the data coming in at the antenna from the wireless connection in a manner that makes the data appear identical to the way the data would flow if using a wired sensor connected to the host device. For example, wired leads may feed the data to the host in a parallel fashion through certain connector device. In some embodiments of the wireless healthcare system, the data may be coming from equivalent wireless micropatches, in a multiplexed fashion over the radio link. In this case, the transcoder can collect the multiple equivalent signals from the micropatches that correspond to the multiple wired sensors of a wired system. The transcoder can then demultiplex the data, or perform any other suitable processing of the data, to convert it to parallel channels that are equivalent to the wired system. In summary, the transcoder will collect the data from the wireless micropatches through the radio as dictated by the radio protocol. The transcoder can then rearrange the data received from the micropatches into a format that the host is used to receiving when attached to wired leads. After the data has been rearranged, the transcoder can then send data to the host interface unit (host I/F), as shown in FIG. 5. The transcoder can also have a digital-to-analog converter to convert the digital stream into one or more analog waveforms that are equivalent to a wired system. The parallel analog waveforms can be fed to the host using the same connector device that is used in the corresponding wired system.

In some embodiments, a stand alone base with a built in radio can be used with a patch comprising a radio system that is different from the built-in radio connectivity of the wireless host device. The base can be designed so that it connects two different radio systems together. The base can receive data from the micropatch using a radio that is compatible with the micropatches. The trans coder can decode and rearrange the received data in a manner consistent with the radio of the host device. The base can then retransmit the data to the host using a radio that is compatible with the device. Similarly, the data can also flow in a reverse path, from the host to the micropatches. The host I/F and connector in the base as shown in FIG. 5 become the radio system of the host device. The base can then communicate with two radio systems. For example, the radio system for the micropatches can be based on ultra-wideband (UWB) or ZigBee and the radio system on the host device can be Bluetooth or WiFi.

The host I/F unit can then transmit the data to the host using the host's bus scheme. In some embodiments, the host bus can be a USB bus. The host bus can be any suitable bus including, but not limited to, USB, Mini USB, secure digital (SD), mini secure digital (Mini SD), PCI, Mini PCI, an analog bus, any suitable standard or proprietary wired bus, or any combination to thereof. The data from the host I/F circuits can then flow to the host through an appropriate connector as shown in FIG. 3. For example purposes only, in an embodiment where a USB bus is used, the connector will be the mechanical USB connector.

In some embodiments, the micropatches can communicate with the base. In some embodiments, the base can communicate with the micropatches. The base can transmit information from the host to the micropatches in a seamless or transparent manner. The host device can initiate measurements in whatever manner the host device uses when wired electrodes are used. The relay device can detect such measurement initiation and send a command to the wireless sensor to start the measurement. The relay device can then get a response from the sensor and relay the response back to the host device. For example purposes only, a patient monitor in the hospital could initiate periodic pulse-oximetry measurements by sending signals through the wires to light LEDs of the pulse-oximetry device attached to a finger, and elicit a response from the photo detector in the device, which then comes back to the monitor through some other wire. The relay station of the device provided herein could then detect the start of such a measurement through its interface to the host device, and send a wireless command to the patch to light up light emitting diodes (LEDs) and collect a response from the photodetector. The response can then be sent back to the relay station, which can then relay the response to a monitor. To the monitor the whole exchange between the base and the sensor would appear as if it had occurred through a wired system. Additionally, the components can perform their functions in reverse order.

The base shown in FIG. 5 can be implemented in a variety of ways. The base can be a dongle or a card that connects to the host device. Alternatively, the base can be a stand-alone module that has one or more cables with connectors that can then be plugged into the host device. The base can have its own power supply. Alternatively, the device can be powered by the host device through the one or more cables. The base can be a component of the host device, wherein the base is housed within the host device. The base can be a wireless stand alone module that connects the patches with the host device wirelessly. The base can exist in any suitable form for transferring data from the patches to the host device.

In some embodiments, the components of the base can comprise off-the-shelf devices. Alternatively, the components of the base can be integrated in an application specific integrated circuit (ASIC) chip.

II. Systems

Further provided herein is a system integrated as at least one application specific integrated circuit for converting a wired sensor system to a wireless sensor system comprising: a relay station adaptable to convert a wired sensor system to a wireless sensor system; and at least one wireless patch comprising a wireless sensor and at least one radio, wherein the relay station is adaptable to convert a wired sensor system to a wireless sensor system. The at least one wireless patch can further comprise an analog to digital converter. In some embodiments, more than one wireless patch can communicate with the relay station, the relay station adaptable to receive more than one signal. The radio can multiplex the more than one signal to transmit the signal.

III. Methods

Methods of detecting a signal are also provided herein. Disclosed is a method of detecting a signal using a wireless sensor system comprising: (a) detecting at least one signal from a signal source; (b) transmitting the signal in digital format to a relay station comprising at least one antenna and at least one radio, the relay station integrated as at least one application specific integrated circuit and further adaptable to convert a wired sensor system into a wireless sensor system; (c) processing the data received with the relay station; and (d) transmitting the processed data to a host device. The at least one signal can be an analog signal. The method can further comprise the step of converting the analog signal to a digital signal prior to the transmitting step. Additionally, the method can further comprise the step of converting the digital signal to an analog signal prior to the transmitting step.

Further provided herein is a method of retrofitting a wired healthcare system into a wireless healthcare system comprising: retrofitting a wired healthcare system with an adapter member in communication with a wired healthcare system, the adapter member comprising at least one antenna and at least one radio, wherein the adapter member is adaptable to be integrated as at least one application specific integrated circuit and further adaptable to convert a wired healthcare system into a wireless healthcare system. The method can further comprise the step of applying at least one wireless patch to a patient, the wireless patch adaptable to detect a physiological parameter and further adaptable to communicate with the adapter member.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for monitoring a physiological parameter of a subject with the aid of a relay station that converts a wired sensor system into a wireless sensor system, comprising:
    a host device configured to monitor said physiological parameter of said subject;
    a relay station that is in communication with said host device wherein said relay station comprises i) at least one antenna, ii) at least one radio coupled to said at least one antenna, and iii) a host interface unit that, with the aid of said at least one radio, transmits data from the relay station to said host device, wherein said relay station is integrated as at least one application specific integrated circuit, and wherein said relay station is configured to convert a wired sensor system into a wireless sensor system; and
    a portable patch that is in wireless communication with said relay station, wherein said portable patch comprises i) at least one antenna, ii) at least one radio coupled to said at least one antenna, iii) at least one sensor, and iv) an application specific integrated circuit coupled to said at least one sensor,
    wherein, with the aid of said at least one sensor, said portable patch collects sensor data from said subject and, with the aid of said at least one radio of said portable patch, transmits said sensor data to said relay station,
    wherein said relay station receives said sensor data from said portable patch, rearranges said sensor data to an analog or digital format, and transmits said sensor data to said host device, and
    wherein said at least one radio of said relay station and said at least one radio of said portable patch are complementary radios such that, upon operation of said at least one radio of said relay station and said at least one radio of said portable patch, power is distributed asymmetrically between said relay station and said portable patch.

2. The system of claim 1 wherein the relay station further comprises a transcoder that demultiplex data received by the relay station into a format recognizable by said host device.

3. The system of claim 1 wherein the host interface unit transmits data from the relay station to the host device using a host device bus scheme.

4. The system of claim 3 wherein the host bus scheme is at least one of a universal serial bus, a mini universal serial bus, a secure digital, a mini secure digital, a peripheral component interconnect, a mini peripheral component interconnect, or an analog bus.

5. The system of claim 1 further comprising a connector to communicate with a host device.

6. The system of claim 5 wherein the connector comprises a bus that is in communication with the host device.

7. The system of claim 1 wherein the relay station further comprises more than one radio.

8. The system of claim 1 wherein the portable patch is integrated with said application specific integrated circuit.

9. The system of claim 1 wherein the relay station transmits data from said host device to said portable patch.

10. The system of claim 1 wherein the relay station uses at least one host radio to wirelessly send data received from said portable patch to said host device having wireless connectivity with the relay station.

11. The system of claim 10 wherein said host radio uses at least one of radio scheme.

12. The system of claim 11 wherein the at least one radio scheme is selected from Wi-Fi, Bluetooth, ZigBee, wireless medical telemetry service, medical implant communications service, a narrowband radio, or an ultrawideband radio.

13. The system of claim 1 wherein the complementary radios are ultrawideband and narrowband radios.

14. The system of claim 1 wherein the complementary radios operate in a low power mode and a high power mode.

15. The system of claim 1 wherein the complementary radios operate in a short range mode and a high range mode.

16. The system of claim 1 wherein the relay station is in communication with two different radios.

17. The system of claim 1 wherein the portable patch further comprises an analog to digital converter.

18. The system of claim 1 further comprising more than one portable patch in communication with the relay station.

19. The system of claim 1 wherein the relay station receives more than one signal.

20. The system of claim 1, wherein said at least one radio of said portable patch comprises a radio containing an ultra wideband (UWB) transmitter and a narrowband receiver.

21. The system of claim 20, wherein said at least one radio of the relay station comprises a UWB receiver and a narrowband transmitter.

22. The system of claim 1, wherein the portable patch is integrated as at least one application specific integrated circuit.

23. A method for monitoring a physiological parameter of a subject, comprising:
    (a) detecting sensor data from said subject with the aid of a portable patch comprising i) at least one antenna, ii) at least one radio coupled to said at least one antenna, iii) at least one sensor, and iv) an application specific integrated circuit coupled to said at least one sensor;
    (b) transmitting the sensor data from said portable patch to a relay station that is in wireless communication with said portable patch, said relay station comprising i) at least one antenna, ii) at least one radio coupled to said at least one antenna, and iii) a host interface unit, wherein the relay station is integrated as at least one application specific integrated circuit, and wherein the relay station is configured to convert a wired sensor system into a wireless sensor system;
    (c) processing the sensor data received with the relay station, said processing comprising rearranging said sensor data to analog or digital format; and
    (d) transmitting the processed data to a host device configured to monitor said physiological parameter of said subject,
    wherein said at least one radio of said relay station and said at least one radio of said portable patch are complementary radios such that, upon operation of said at least one radio of said relay station and said at least one radio of said portable patch, power is distributed asymmetrically between said relay station and said portable patch.

24. The method of claim 23 wherein the sensor data comprises at least one signal that is an analog signal.

25. The method of claim 24 further comprising the step of converting the analog signal to a digital signal prior to step (b).

26. The method of claim 23 further comprising the step of converting the digital signal to an analog signal prior to step (d).

27. The method of claim 23, wherein processing the data in (c) comprises rearranging the data received from the patch into a format that is readable by the host device.

28. The method of claim 23, wherein the portable patch is integrated as at least one application specific integrated circuit.

29. The method of claim 23, wherein the relay station uses at least one host radio to wirelessly send data received from said portable patch to said host device having wireless connectivity with the relay station.

30. The method of claim 29, wherein said host radio uses at least one of radio scheme selected from Wi-Fi, Bluetooth, ZigBee, wireless medical telemetry service, medical implant communications service, a narrowband radio, and an ultrawideband radio.

31. The method of claim 23, wherein said at least one radio of said portable patch comprises a radio containing an ultra wideband (UWB) transmitter and a narrowband receiver.

32. The method of claim 31, wherein said at least one radio of said relay station comprises a UWB receiver and a narrowband transmitter.

33. The method of claim 23 further comprising applying said portable patch to said subject prior to (a).

* * * * *

UNITED STATES PATENT AND TRADEMARK OFFICE
CERTIFICATE OF CORRECTION

PATENT NO. : 8,611,319 B2  Page 1 of 1
APPLICATION NO. : 12/739519
DATED : December 17, 2013
INVENTOR(S) : Magar et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 329 days.

Signed and Sealed this
Twenty-second Day of September, 2015

Michelle K. Lee
*Director of the United States Patent and Trademark Office*